(12) United States Patent
Huxford et al.

(10) Patent No.: US 9,265,698 B2
(45) Date of Patent: Feb. 23, 2016

(54) HOUSING FOR AN ORAL HYGIENE AND MEDICATION DEVICE, AND AN ASSEMBLY THEREOF

(75) Inventors: Catherine Maria Huxford, Wellington (NZ); Bradley Allan James Brown, Wellington (NZ); Peter John Wilcock, Wellington (NZ); Jon Leonard Fifield, Wellington (NZ)

(73) Assignee: ISSACHAR LIMITED, Auckland (NZ)

( * ) Notice: Subject to any disclaimer, the term of this patent is extended or adjusted under 35 U.S.C. 154(b) by 52 days.

(21) Appl. No.: 14/233,716

(22) PCT Filed: Jul. 27, 2012

(86) PCT No.: PCT/NZ2012/000130
§ 371 (c)(1),
(2), (4) Date: Jan. 21, 2014

(87) PCT Pub. No.: WO2013/015695
PCT Pub. Date: Jan. 31, 2013

(65) Prior Publication Data
US 2014/0202918 A1   Jul. 24, 2014

(30) Foreign Application Priority Data
Jul. 28, 2011 (NZ) ........................................ 594300

(51) Int. Cl.
*B65D 69/00*   (2006.01)
*A61J 1/22*    (2006.01)
(Continued)

(52) U.S. Cl.
CPC . *A61J 1/22* (2013.01); *A46B 17/04* (2013.01); *A47K 1/09* (2013.01); *A61M 15/009* (2013.01);
(Continued)

(58) Field of Classification Search
CPC ... A61F 17/00; A47K 1/09; A61M 2209/082; A61M 2205/6045
USPC ......... 206/570, 229, 363, 370, 368, 361, 438, 206/528, 538, 362.1, 362.2; 132/308; 211/65, 66
See application file for complete search history.

(56) References Cited

U.S. PATENT DOCUMENTS 2,997,210 A * 8/1961 MacKirdy ........................ 222/93
3,977,743 A * 8/1976 Harris ............................ 312/207
(Continued)

FOREIGN PATENT DOCUMENTS

NZ   314244   3/1999
NZ   536176   4/2007
(Continued)

OTHER PUBLICATIONS

Kolbe, Asthma education, action plans, psychosocial issues and adherence, Can Respir J, vol. 6, No. 3, May/Jun. 1999, pp. 273-280.
(Continued)

*Primary Examiner* — Jacob K Ackun
*Assistant Examiner* — Jenine Pagan
(74) *Attorney, Agent, or Firm* — Squire Patton Boggs (US) LLP

(57) ABSTRACT

The invention provides a housing adapted to provide for the juxtaposition of an oral hygiene device, such as a toothbrush, with an inhaler medication device, such as a metered dose inhaler (MDI) or dry powder inhaler (DPI). Also provided is an assembly including a housing, an oral hygiene device and an inhaler medication device wherein, in use, the housing and inhaler medication device together secure the oral hygiene device in the housing such that the oral hygiene device cannot be removed for use without first removing the inhaler medication device.

11 Claims, 9 Drawing Sheets

(51) Int. Cl.
*A61M 15/00* (2006.01)
*A46B 17/04* (2006.01)
*A47K 1/09* (2006.01)

(52) U.S. Cl.
CPC .... *A61M 15/0025* (2014.02); *A46B 2200/1066* (2013.01); *A61M 2205/58* (2013.01); *A61M 2205/6045* (2013.01); *A61M 2209/082* (2013.01)

(56) References Cited

U.S. PATENT DOCUMENTS

| | | | | |
|---|---|---|---|---|
| 4,396,238 | A | * | 8/1983 | Torruella ................ 312/206 |
| 4,964,683 | A | | 10/1990 | Sugarek |
| 5,839,578 | A | | 11/1998 | Avery |
| 5,855,307 | A | | 1/1999 | Biddick |
| 5,890,605 | A | * | 4/1999 | Percudani ............... 211/87.01 |
| 5,960,801 | A | | 10/1999 | Vermooten |
| 6,053,338 | A | | 4/2000 | Avery |
| 6,325,222 | B1 | | 12/2001 | Avery |
| 7,753,197 | B2 | * | 7/2010 | Russell .................... 206/228 |
| 2002/0100490 | A1 | * | 8/2002 | Bodwalk .................. 132/309 |
| 2004/0238701 | A1 | * | 12/2004 | Nanda ..................... 248/206.4 |
| 2005/0030163 | A1 | | 2/2005 | Shiner |
| 2005/0268935 | A1 | | 12/2005 | Hoffecker |
| 2006/0059643 | A1 | | 3/2006 | Jimenez |
| 2007/0114891 | A1 | * | 5/2007 | Kim ........................ 312/207 |
| 2007/0158518 | A1 | * | 7/2007 | Kurdoghlian ............ 248/312 |
| 2008/0230057 | A1 | | 9/2008 | Sutherland |
| 2010/0192948 | A1 | | 8/2010 | Sutherland |

FOREIGN PATENT DOCUMENTS

| | | |
|---|---|---|
| WO | WO 03/012756 | 2/2003 |
| WO | WO 2008/030804 | 3/2008 |
| WO | WO 2008/030814 | 3/2008 |
| WO | WO 2008/030829 | 3/2008 |
| WO | WO 2011/061536 | 5/2011 |

OTHER PUBLICATIONS

International Search Report for PCT/NZ2012/000130.

* cited by examiner

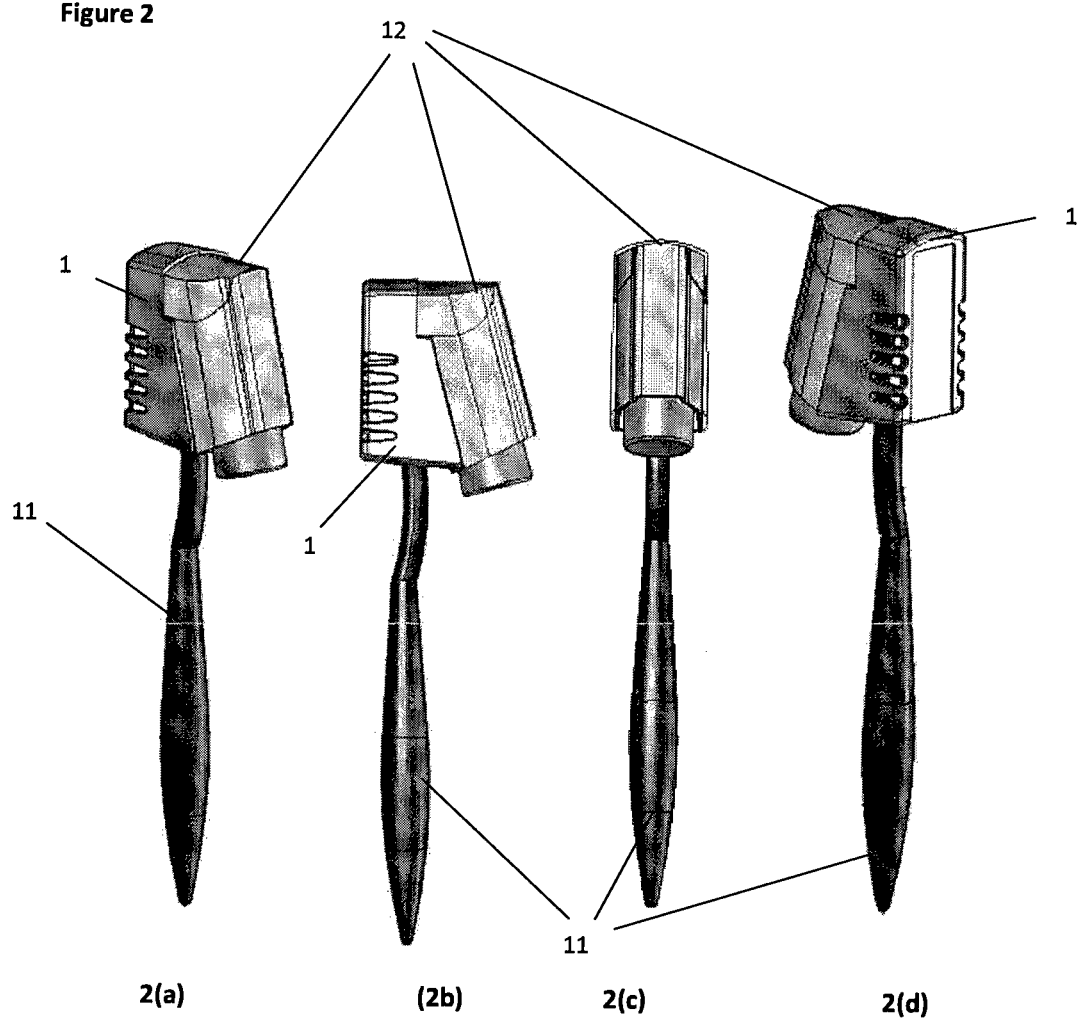

Figure 3 (a)
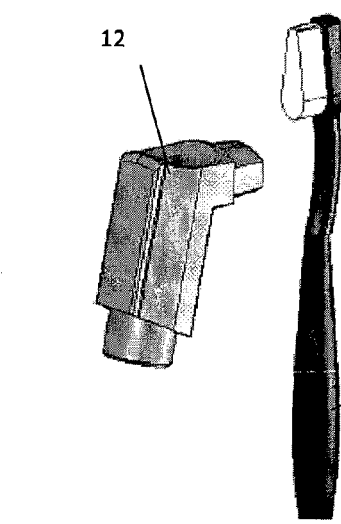
Figure 3(b)
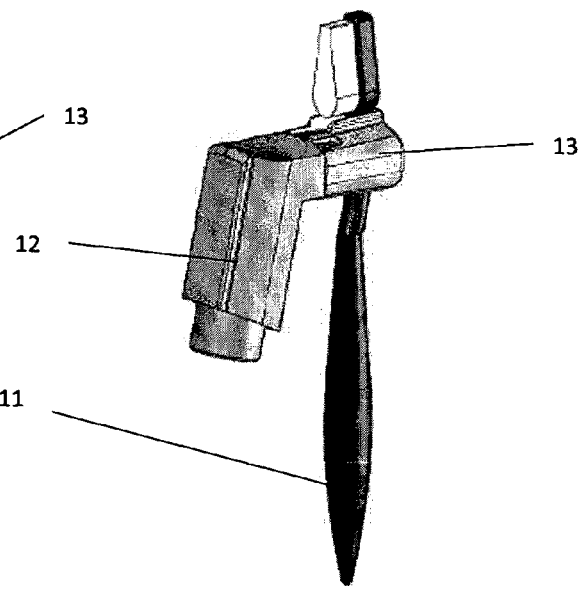
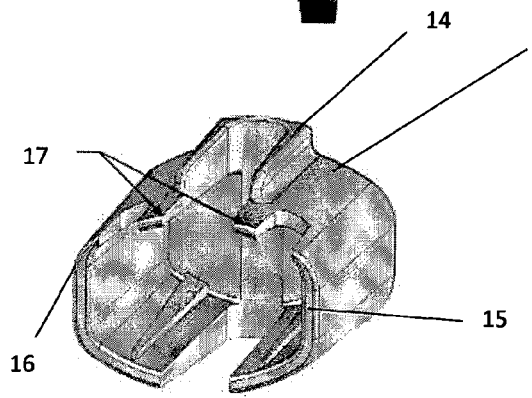
Figure 3(c)
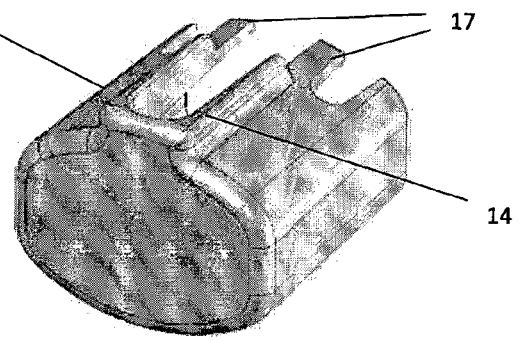
Figure 3(d)
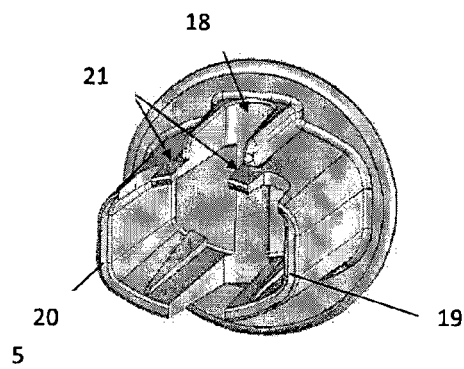
Figure 3(e)
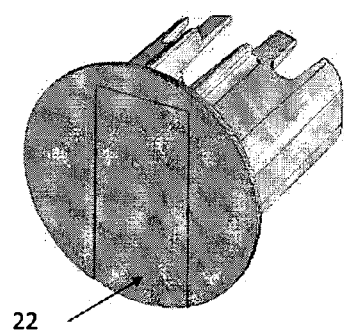
Figure 3(f)

Figure 5(a)
Figure 5(b)
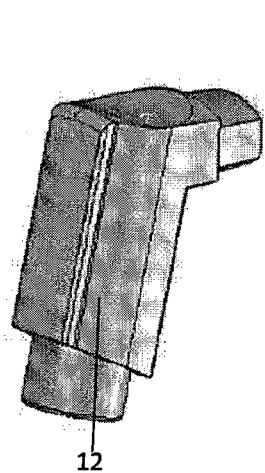
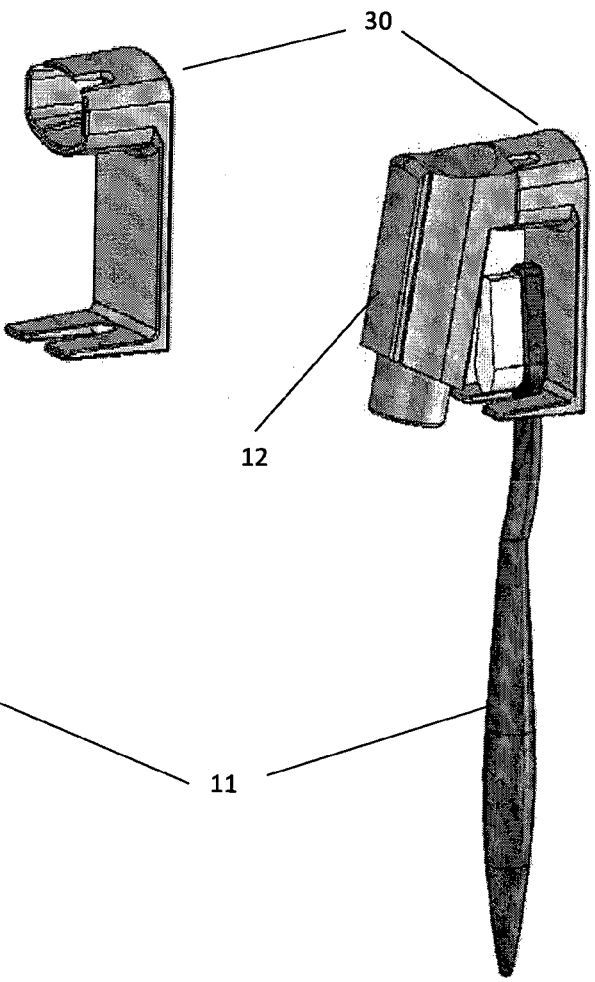
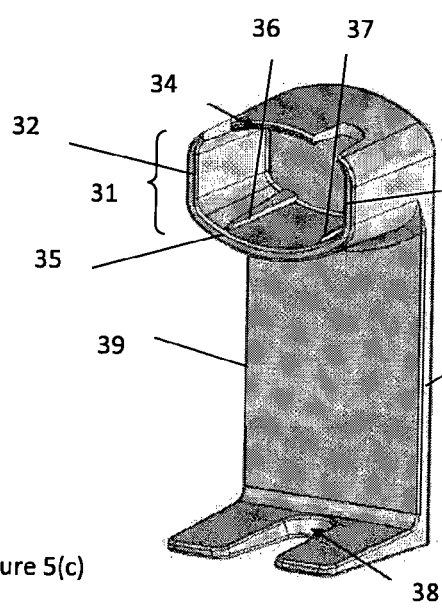
Figure 5(c)
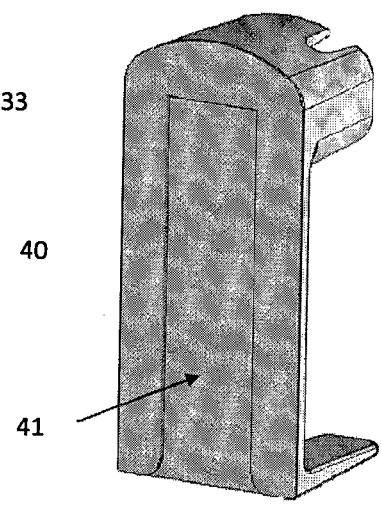
Figure 5(d)

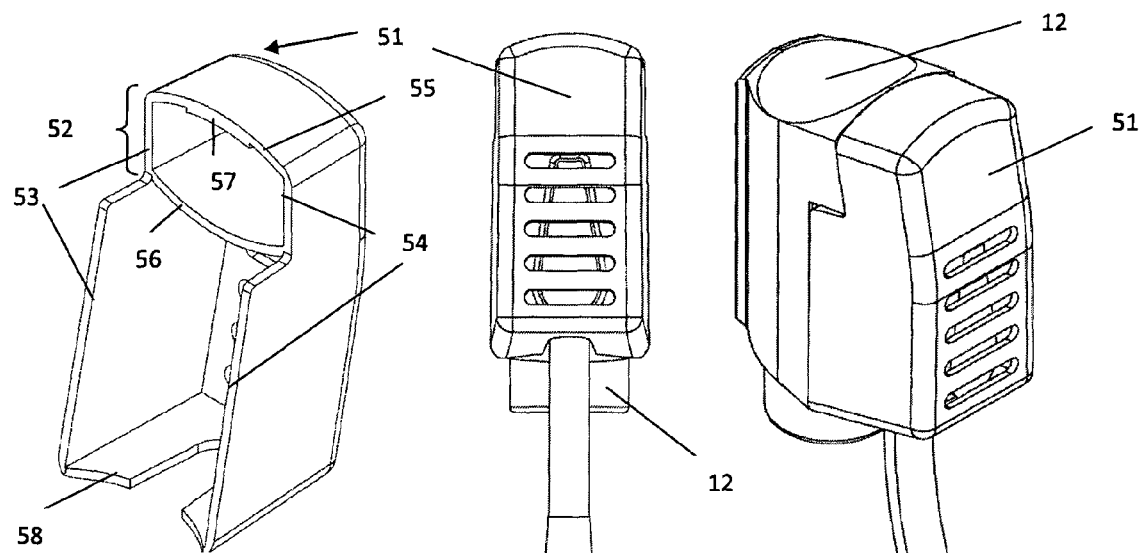
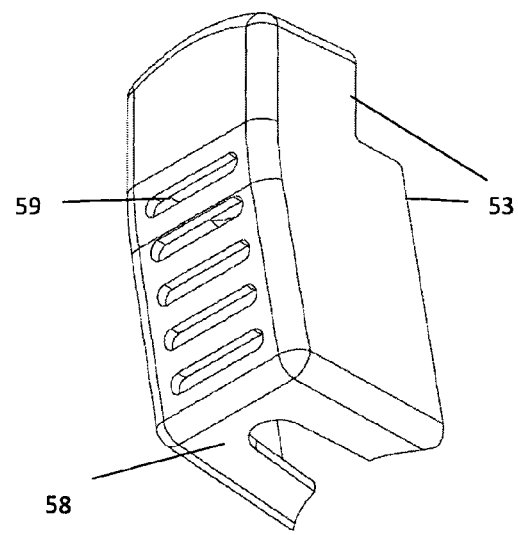
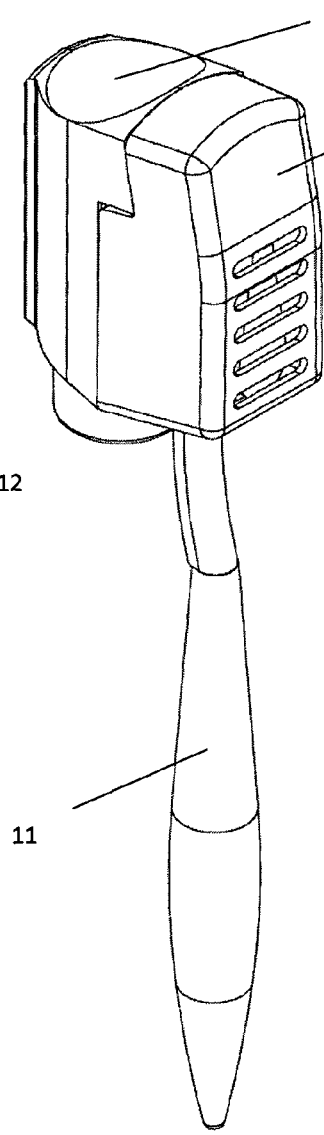
Figure 7(a)
Figure 7(b)    Figure 7(c)    Figure 7(d)

HOUSING FOR AN ORAL HYGIENE AND MEDICATION DEVICE, AND AN ASSEMBLY THEREOF

TECHNICAL FIELD OF THE INVENTION

The present invention relates to a housing adapted to provide for the juxtaposition of an oral hygiene device, such as a toothbrush, with an inhaler medication device, such as a metered dose inhaler (MDI) or dry powder inhaler (DPI). Also provided is an assembly including a housing, an oral hygiene device and an inhaler medication device.

BACKGROUND OF THE INVENTION

Asthma and other respiratory diseases, such as chronic obstructive pulmonary disease (COPD) have long been treated by the delivery via inhalation of appropriate medication into the body via the lungs. The inhalation of the medication has been facilitated by an inhaler or puffer device. For many years the two most widely used and convenient choices of portable treatment devices have been the metered dose pressurised inhaler (MDI), or a dry powder inhaler (DPI). In an MDI the medication is most commonly stored in solution in a pressurised canister that contains a propellant, although the medication may also be in suspension. The MDI canister is attached to a plastic, hand-operated actuator. On activation, the MDI releases a fixed dose of medication in aerosol form from the mouthpiece of the MDI that can then be drawn into the lungs of the user. Dry powder inhalers release a dose of the medication as a powder aerosol.

In medicine, compliance or adherence describes the degree to which a patient correctly follows medical advice. Non-compliance or non-adherence of patients in taking their medication is a major recognised problem in the effective delivery of health care. Estimates from the World Health Organisation indicate that asthma non-compliance could be as significant as 28-70% worldwide, which means that there is a corresponding increase in the risk of severe asthma attacks requiring hospitalisation and this contributes to the human and economic burden of asthma as a condition. Non-adherence of asthma sufferers to their medication in the US alone is estimated to cost US $290 million per year. One of the major compliance barriers seen in asthma sufferers not taking their medication or overusing the wrong type of asthma medication is the difficulty for asthma sufferers to habitually remember to take their preventive medication. The preventive medication, such as Seretide® made by GlaxoSmithKline that includes fluticasone proprionate (a preventer of asthma symptoms) with salmeterol (an asthma symptom controller), needs to be taken on a twice daily basis. Efforts to improve compliance with asthma sufferers taking their preventive medication that are undertaken include the likes of sending reminders including telephone reminders, using individualised charts, diaries, e-mail, text or SMS messages, electronic applications for use with smartphones and the like. However, all of these efforts or systems require ongoing costs and daily interruption in the lives of asthma sufferers.

The present invention aims to provide an alternative low cost method of providing a device that reminds an asthma sufferer to use their inhaler every time that they brush their teeth, or to at least provide the public with a useful choice.

SUMMARY OF THE INVENTION

In a first aspect the present invention provides a housing that is adapted to, in use, receive an oral hygiene device and an inhaler medication device having a mouthpiece, wherein, in use, the housing and inhaler medication device together secure the oral hygiene device in the housing such that the oral hygiene device cannot be removed for use without first removing the inhaler medication device.

In one embodiment the housing includes a first bracket portion that, in use, receives the oral hygiene device and a second engagement portion for receiving the inhaler medication device, wherein in use the second engagement portion engages the mouthpiece of the inhaler medication device.

In another embodiment the second engagement portion is adapted in size and shape to substantially surround the mouthpiece of the inhaler upon engagement with the inhaler medication device. In a preferred embodiment the second engagement portion is adapted to provide a snap fit engagement with the mouthpiece of the inhaler medication device.

In a further embodiment the housing is further adapted to substantially surround the head of the oral hygiene device when the oral hygiene device is in situ on the first bracket portion.

In another embodiment the housing is further adapted to provide ventilation slots to allow air circulation around the head of the oral hygiene device.

In a further embodiment the housing is adapted to include or receive an attachment means to enable attachment of the housing to an attachment surface. In one embodiment the attachment means may include a rebate region to apply an adhesive strip to the housing. In another embodiment the housing is adapted to be reversibly attached to a separate attachment member and wherein the separate attachment member is further adapted to be mounted to an attachment surface.

In a further embodiment the inhaler medication device is a metered dose inhaler (MDI).

In a second aspect of the invention there is provided an assembly including a housing, an oral hygiene device and an inhaler medication device, wherein the housing and inhaler medication device together secure the oral hygiene device in the housing such that in use the oral hygiene device cannot be removed from the assembly without first removing the inhaler medication device.

It is to be appreciated that the assembly described above can include any of the embodiments of the housing aspect described above.

The foregoing brief summary broadly describes the features and technical advantages of certain embodiments of the present invention. Further technical advantages will be described in the detailed description of the invention that follows. Novel features which are believed to be characteristic of the invention will be better understood from the detailed description of the invention when considered in connection with any accompanying figures and examples. However, the figures and examples provided herein are intended to help illustrate the invention or assist with developing an understanding of the invention, and are not intended to be definitions of the invention's scope.

BRIEF DESCRIPTION OF THE DRAWINGS

FIG. 2(a) shows a front perspective view of an assembly including the first embodiment of a housing supporting an oral hygiene device and engaging an inhaler medication device.

FIG. 2(b) shows a side view of an assembly including the first embodiment of a housing supporting an oral hygiene device and engaging an inhaler medication device.

FIG. 2(c) shows a front view of an assembly including the first embodiment of a housing supporting an oral hygiene device and engaging an inhaler medication device.

FIG. 2(d) shows a rear perspective view of an assembly including the first embodiment of a housing supporting an oral hygiene device and engaging an inhaler medication device.

FIG. 3(a) shows a spaced apart relationship between a second embodiment of a housing for use with an oral hygiene device and an inhaler medication device.

FIG. 3(b) shows an assembly of a second embodiment of a housing with an oral hygiene device and an inhaler medication device.

FIG. 3(c) shows a front perspective view of a second embodiment of a housing shown in FIGS. 3(a) and 3(b).

FIG. 3(d) shows a rear perspective view of a second embodiment of a housing shown in FIGS. 3(a) and 3(b).

FIG. 3(e) shows a front perspective view of a third embodiment of a housing for use with an oral hygiene device and an inhaler medication device.

FIG. 3(f) shows a rear perspective view of a third embodiment of a housing for use with an oral hygiene device and an inhaler medication device.

FIG. 5(a): shows a spaced apart relationship between a fifth embodiment of a housing for use with an oral hygiene device and an inhaler medication device.

FIG. 5(b) shows an assembly of a fifth embodiment of a housing with an oral hygiene device and an inhaler medication device.

FIG. 5(c) shows a front perspective view of a fifth embodiment of a housing shown in FIGS. 5(a) and 5(b).

FIG. 5(d) shows a rear perspective view of a fifth embodiment of a housing shown in FIGS. 5(a) and 5(b).

FIG. 7(a) shows a front view of a seventh embodiment of a housing for use with an oral hygiene device and an inhaler medication device.

FIG. 7(b) shows a rear perspective view of a seventh embodiment of a housing for use with an oral hygiene device and an inhaler medication device.

FIG. 7(c) shows a rear view of an assembly of a seventh embodiment of a housing shown with an oral hygiene device and an inhaler medication device.

FIG. 7(d) shows a front perspective view of a seventh embodiment of a housing shown with an oral hygiene device and an inhaler medication device.

FIG. 10 (d) shows a side view of the eighth embodiment of the housing shown in FIG. 10(b) partly disengaged from the attachment means on an attachment surface.

FIG. 10 (e) shows a side view of the eighth embodiment of the housing shown in FIG. 10(b) disengaged from the attachment means on an attachment surface.

DETAILED DESCRIPTION OF THE INVENTION

Prior to setting forth the invention in detail, it may be helpful to provide definitions of certain terms to be used herein. Unless defined otherwise, all technical and scientific terms used herein have the same meaning as is commonly understood by one of skill in the art to which this invention belongs.

DEFINITIONS

An "oral hygiene device" is to be understood as including a toothbrush that is used to clean the teeth and gums that consists of a head of bristles mounted on a handle. The head of bristles may be optionally powered.

An "an inhaler medication device" is to be understood as including the most commonly used type of inhalers, typically a metered dose inhaler, and a dry powder inhaler.

A "metered dose inhaler" or MDI consists of a pressurised canister, where the specific medication and inactive gas to propel the medication resides; a metering valve, which allows a metered quantity of the formulation to be dispensed with each actuation; and a mouthpiece (or actuator) which allows the patient to operate the device and directs the aerosol into the patient's lungs.

A "dry powder inhaler" or DPI consists of a canister where the specific dry powdered medication resides and a mouthpiece. A DPI does not contain a pressurised inactive gas to propel the medication. Instead a user triggers a dose of medication by breathing in (inhaling) at the mouthpiece to effectively suck the powder into the lungs of the user.

Figure 1A:
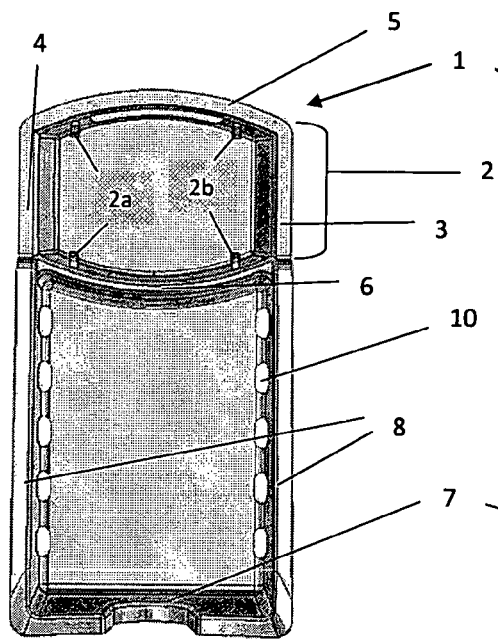
FIG. 1(a) shows a front view of a first embodiment of a housing for use with an oral hygiene device and an inhaler medication device.
Figure 1B:
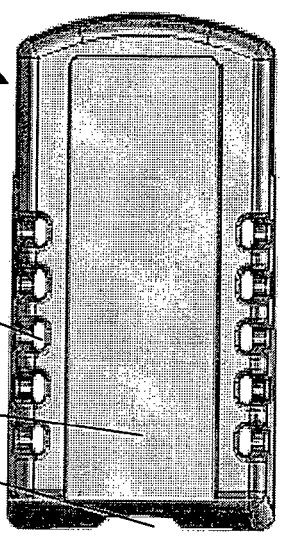
FIG. 1(b) shows a rear view of a first embodiment of a housing for use with an oral hygiene device and an inhaler medication device.
Figures 1C, 1D:
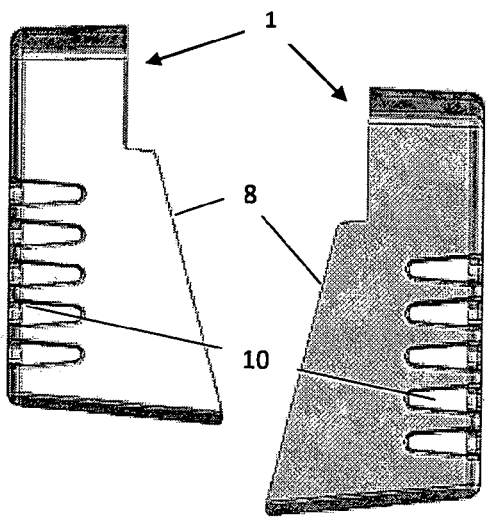
FIGS. 1(c) and 1(d) each show a side view of a first embodiment of a housing for use with an oral hygiene device and an inhaler medication device.
Figures 1E, 1F:
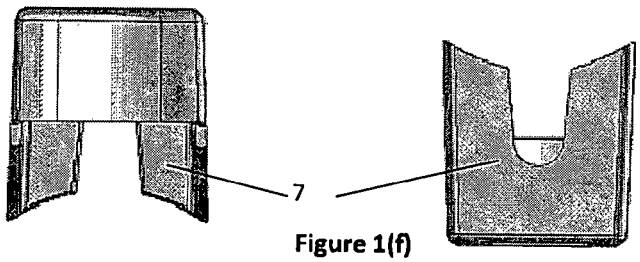
FIG. 1(e) shows a top view of a first embodiment of a housing for use with an oral hygiene device and an inhaler medication device.
FIG. 1(f) shows a bottom view of a first embodiment of a housing for use with an oral hygiene device and an inhaler medication device.

As shown in FIGS. 1(a) to 1(f) various representations of a first embodiment of a housing 1 of the invention are depicted. In FIG. 1(a) the front view shows the engagement portion 2 of the housing that in use engages with the mouthpiece of an inhaler. The engagement portion 2 is defined by a first side Sand a second side 4, a top side 5 and bottom side 6 and engagement ribs 2a and 2b. The engagement ribs 2a and 2b allow for a snap fit engagement with the mouthpiece of an inhaler. A bracket portion 7 supports the head of an oral hygiene device when the housing is in use. The handle of the oral hygiene device extends beneath the bracket portion of the housing. The bracket portion 7 is spaced apart from the engagement portion 2 to allow for the accommodation of the head of an oral hygiene device (not shown). FIGS. 1(c) and 1(d) show the left and right side views respectively of the housing 1. The sides 8 that extend from the top of the engagement portion 2 to the bracket portion 7 are shaped to complement the shape of the inhaler device so that in use the housing (i) substantially encloses the mouthpiece of the inhaler and (ii) substantially encloses the head of the oral hygiene device. A rear view of the housing is shown in FIG. 1(b) and an optional rebate area 9 is shown along which an adhesive pad can be attached to secure the housing to a surface (not shown). The FIGS. 1(a), 1(b), 1(c) and 1(d) also show a series of ventilation slots 10 that allow air flow and circulation through the lower portion of the housing that supports the head of the oral hygiene device. FIGS. 1(e) and 1(f) show the top and bottom views of the housing 1 respectively. The shape of the bracket portion 7 of the housing 1 that supports the head of the oral hygiene device is shown.

FIGS. 2(a) to 2(d) show various views of an assembly of the first embodiment of a housing 1 with a toothbrush 11 and an inhaler 12. The assembly views show that the head of the toothbrush is enclosed and secured by the engagement of the inhaler and the housing. In order to use the toothbrush the inhaler must be removed first from the assembly.

FIGS. 3(a) to 3(d) show a second embodiment of a housing 13. The housing 13 is adapted in size and shape to support a toothbrush 11 and to engage with an inhaler 12. The housing 13 however in this embodiment does not enclose the head of the toothbrush. The assembly view shows however, that in order to use or remove the toothbrush the inhaler must be removed first from the assembly.

FIGS. 3(c) and 3(d) show more detail as to the nature of the housing 13. The bracket 14 that supports the head of the toothbrush, when in use, is positioned in this second embodiment above the engagement portion that in use engages with the mouthpiece of the inhaler. The engagement portion is defined by sides 15 and 16 and lugs 17 that are adapted to snap engage with the mouthpiece of the inhaler.

FIGS. 3(e) and 3(f) show a third embodiment of the housing. This third embodiment is closely related to the second embodiment shown in FIGS. 3(a) to 3(d). The bracket 18 that supports the head of the toothbrush, when in use, is also positioned in this third embodiment above the engagement portion that in use engages with the mouthpiece of the inhaler. The engagement portion is defined by sides 19 and 20 and lugs 21 that are adapted to snap engage with the mouthpiece of the inhaler. FIG. 3(f) shows a rebate 22 along the rear of the housing and along which an adhesive pad can be attached to secure the housing to a surface (not shown).

Figures 4A, 4B, 4C:
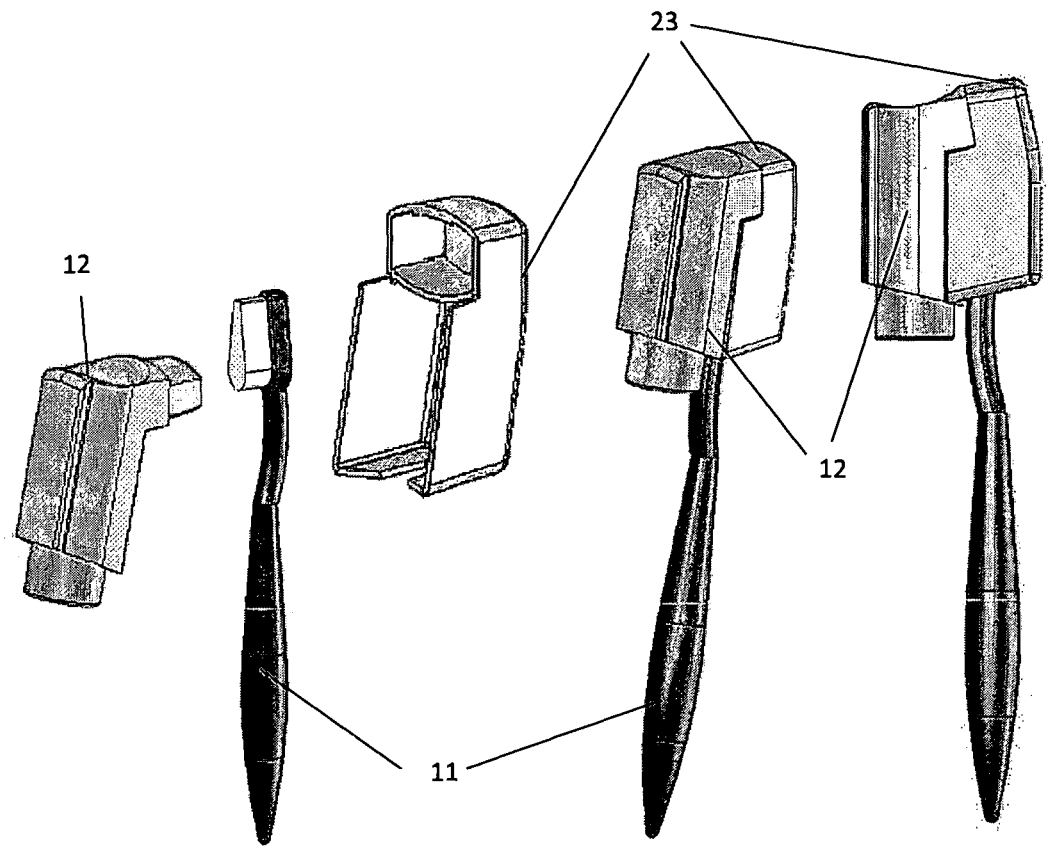
FIG. 4(a) shows a spaced apart relationship between a fourth embodiment of a housing for use with an oral hygiene device and an inhaler medication device.
FIG. 4(b) shows a front perspective view of an assembly of a fourth embodiment of a housing with an oral hygiene device and an inhaler medication device.
FIG. 4(c) shows a side view of an assembly of a fourth embodiment of a housing with an oral hygiene device and an inhaler medication device.

FIGS. 4(a) to 4(c) show a fourth embodiment of a housing 23. The housing 23 is adapted in size and shape to support a toothbrush 11 and to engage with an inhaler 12 in an assembly as shown in FIGS. 4(b) and 4(c). The housing 23 in this embodiment does enclose the head of the toothbrush. The assembly views shows that in order to use or remove the toothbrush the inhaler must be removed first from the assembly.

Figures 4D, 4E:
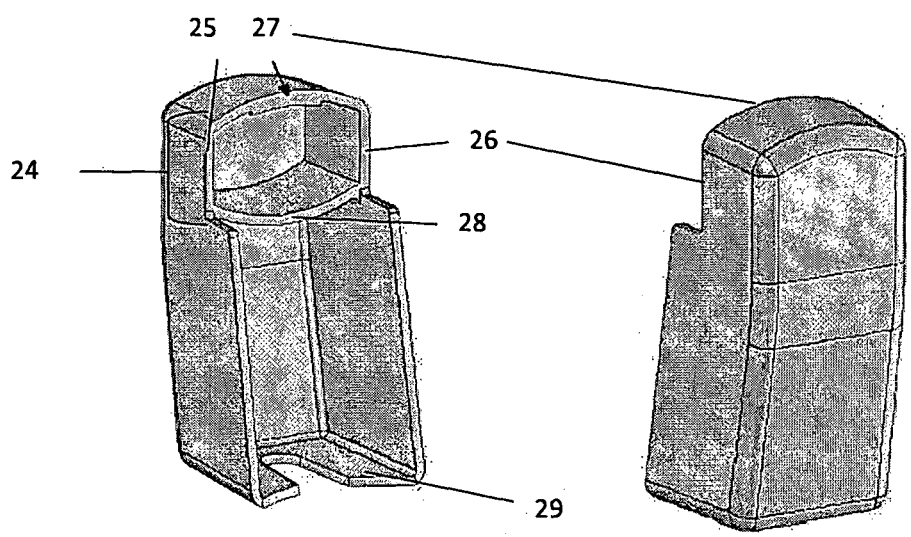
FIG. 4(d) shows a front perspective view of a fourth embodiment of a housing shown in FIGS. 4(a) and 4(b).
FIG. 4(e) shows a rear perspective view of a fourth embodiment of a housing shown in FIGS. 4(a) and 4(b).

FIGS. 4(d) and 4(e) show more detail as to the nature and shape of the housing 23. In FIG. 4(d) the front view shows the engagement portion 24 of the housing that in use engages with the mouthpiece of an inhaler. The first engagement portion 24 is defined by first and second sides 25 and 26, a top side 27 and a bottom side 28. A bracket portion 29 supports the head of an oral hygiene device when the housing is in use. In this embodiment the bracket portion 29 is spaced apart from the engagement portion 24 to allow for the accommodation of the head of an oral hygiene device as shown in FIG. 4(b). The sides 25 and 26 that extend from the top of the engagement portion 24 to the bracket portion 29 are shaped to complement the shape of the inhaler device so that in use the housing (i) substantially encloses the mouthpiece of the inhaler and (ii) substantially encloses the head of the oral hygiene device as shown in FIGS. 4(b) and 4(c).

FIGS. 5(a) to 5(d) show a fifth embodiment of a housing 30. The housing 30 is adapted in size and shape to support a toothbrush 11 and to engage with an inhaler 12. The housing 30 however does not enclose the head of the toothbrush in this embodiment, but the toothbrush is supported below the inhaler. The assembly view in 5(b) shows that in order to use or remove the toothbrush the inhaler must be removed first from the assembly.

FIGS. 5(c) and 5(d) show more detail as to the nature and shape of the housing 30. In FIG. 5(c) the front view shows the engagement portion 31 of the housing that in use engages with the mouthpiece of an inhaler. The engagement portion 31 is defined by first and second sides 32 and 33, a top side 34 and a bottom side 35 and engagement ribs 36 and 37. The engagement ribs 36 and 37 allow for a snap fit engagement with the mouthpiece of an inhaler. A bracket portion 38 supports the head of an oral hygiene device when the housing is in use. In this embodiment the bracket portion 38 is spaced apart from the engagement portion 31 to allow for the accommodation of the head of an oral hygiene device as shown in FIG. 5(b). The sides 39 and 40 that extend from the top of the engagement portion 31 to the bracket portion 38 in this embodiment do not complement the shape of the body of the inhaler device so that in use the housing substantially encloses the mouthpiece of the inhaler but does not enclose the head of the oral hygiene device as shown in FIG. 5(b). FIG. 5(d) shows a rebate 41 along the rear of the housing and along which an adhesive pad can be attached to secure the housing to a surface (not shown).

Figures 6A, 6B, 6C:
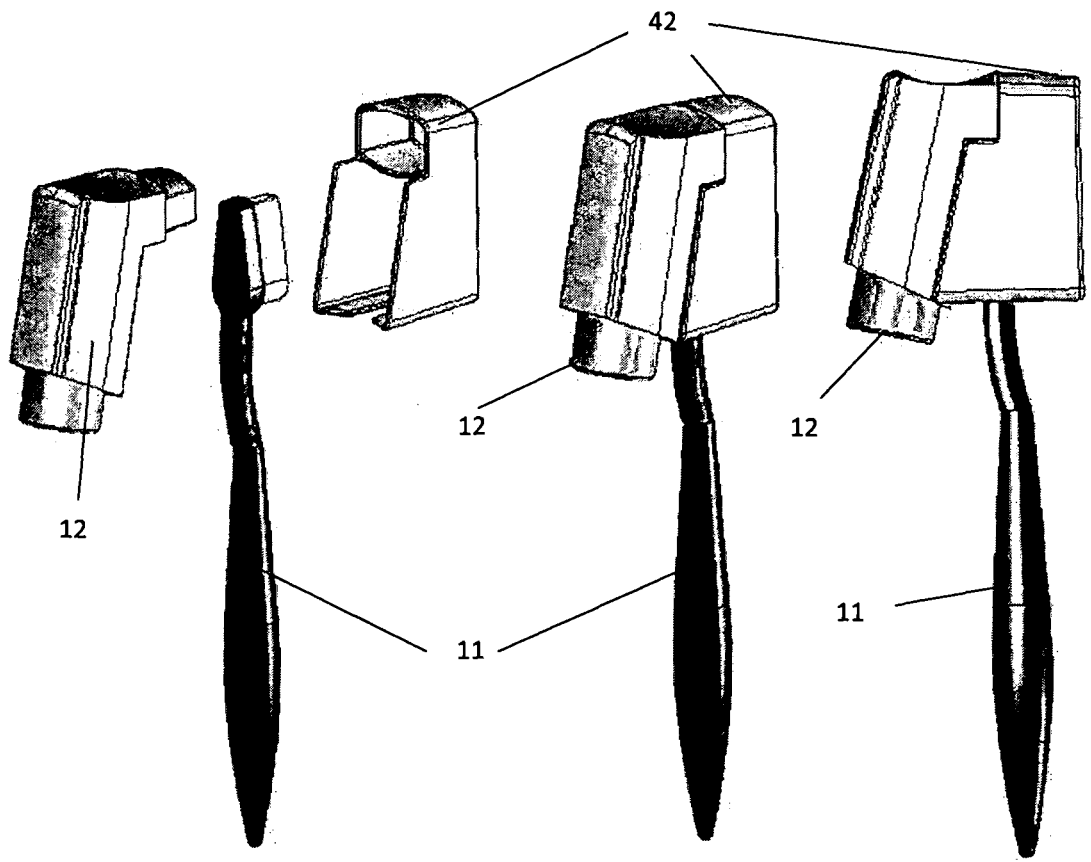
FIG. 6(a): shows a spaced apart relationship between a sixth embodiment of a housing for use with an oral hygiene device and an inhaler medication device.
FIG. 6(b) shows a front perspective view of an assembly of a sixth embodiment of a housing with an oral hygiene device and an inhaler medication device.
FIG. 6(c) shows a side view of an assembly of a sixth embodiment of a housing with an oral hygiene device and an inhaler medication device.

FIGS. 6(a) to 6(c) show a sixth embodiment of a housing 42. The housing 42 is adapted in size and shape to support a toothbrush 11 and to engage with an inhaler 12 in an assembly as shown in FIGS. 6(b) and 6(c). The housing 42 in this embodiment does enclose the head of the toothbrush. The assembly views shown in 6(b) and 6(c) show that in order to use or remove the toothbrush the inhaler must be removed first from the assembly.

Figures 6D, 6E:
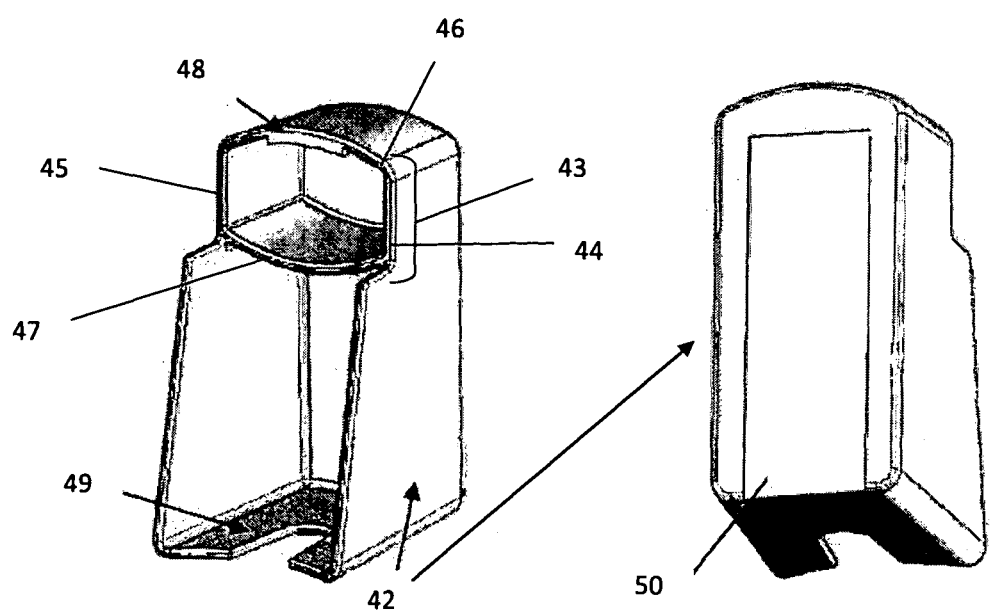
FIG. 6(d) shows a front perspective view of a sixth embodiment of a housing shown in FIGS. 6(a), 6(b) and 6(c).
FIG. 6(e) shows a rear perspective view of a sixth embodiment of a housing shown in FIGS. 6(a), 6(b) and 6(c).
Figure 9A:
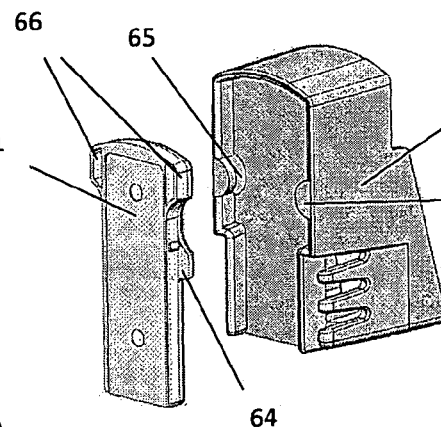
FIG. 9(a) shows a rear perspective view of an eighth embodiment of a housing for use with an oral hygiene device and an inhaled medication device along with a corresponding separate attachment means.

FIGS. 6(d) and 6(e) show more detail as to the nature and shape of the housing 42. In FIG. 6(d) the front view shows the engagement portion 43 of the housing that in use engages with the mouthpiece of an inhaler. The engagement portion 43 is defined by first and second sides 44 and 45, a top side 46 and a bottom side 47 along with an engagement rib 48 to allow for a snap-fit engagement with the mouth piece of the inhaler. A bracket portion 49 supports the head of an oral hygiene device when the housing is in use. In this embodiment the bracket portion 49 is spaced apart from the engagement portion 43 to allow for the accommodation of the head of an oral hygiene device as shown in FIG. 6(b) and FIG. 6(c). The sides 44 and 45 that extend from the top of the engagement portion 43 to the bracket portion 49 are shaped to complement the shape of the inhaler device so that in use the housing (i) substantially encloses the mouthpiece of the inhaler and (ii) substantially encloses the head of the oral hygiene device as shown in FIGS. 6(b) and 6(c). FIG. 6(d) shows a rebate 50 along the rear of the housing and along which an adhesive pad can be attached to secure the housing to a surface (not shown).

FIGS. 7(a) to 7(d) show a seventh embodiment of a housing 51. The housing 51 is adapted in size and shape to support a toothbrush 11 and to engage with an inhaler 12 in an assembly as shown in FIGS. 7(c) and 7(d). The housing 51 in this embodiment does enclose the head of the toothbrush. The assembly views shown in 7(d) shows that in order to use or remove the toothbrush the inhaler must be removed first from the assembly.

FIGS. 7(a) and 7(b) show more detail as to the nature and shape of the housing 51. In FIG. 7(a) the front view shows the engagement portion 52 of the housing that in use engages with the mouthpiece of an inhaler. The engagement portion 52 is defined by first and second sides 53 and 54, a top side 55 and a bottom side 56 along with an engagement rib 57 to allow for a snap-fit engagement with the mouth piece of the inhaler. A bracket portion 58 supports the head of an oral hygiene device when the housing is in use. In this embodiment the bracket portion 58 is spaced apart from the engagement portion 52 to allow for the accommodation of the head of an oral hygiene device as shown in FIG. 7(c) and FIG. 7(d). The sides 53 and 54 that extend from the top of the engagement portion 52 to the bracket portion 58 are shaped to complement the shape of the inhaler device so that in use the housing (i) substantially encloses the mouthpiece of the inhaler and (ii) substantially encloses the head of the oral hygiene device as shown in FIGS. 7(c) and 7(d). It is further shown in this embodiment that a series of spaced apart ventilation slots 59 are provided on the rear of the housing to allow for air circulation around the head of the toothbrush when the toothbrush is located within the housing.

FIGS. 8(a) to 8(c), FIGS. 9(a) to 9(c) and FIGS. 10(a) to 10(e) show an eighth embodiment of the housing 60. Again the housing is adapted in size and shape to support a toothbrush 11 and to engage with an inhaler 12 in an assembly as shown in FIGS. 10(a) to 10(e). The housing 60 in this embodiment does enclose the head of the toothbrush. The assembly views shown in FIGS. 10(a) to 10(e) shows that in order to use or remove the toothbrush the inhaler must be removed first from the assembly.

Figure 8A:
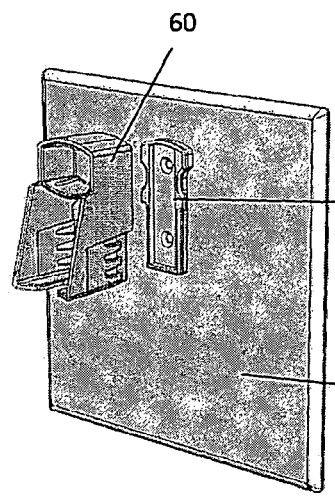
FIG. 8(a) shows a front perspective view of an eighth embodiment of a housing for use with an oral hygiene device and an inhaled medication device along with a separate corresponding attachment means in place on an attachment surface.
Figure 8B:
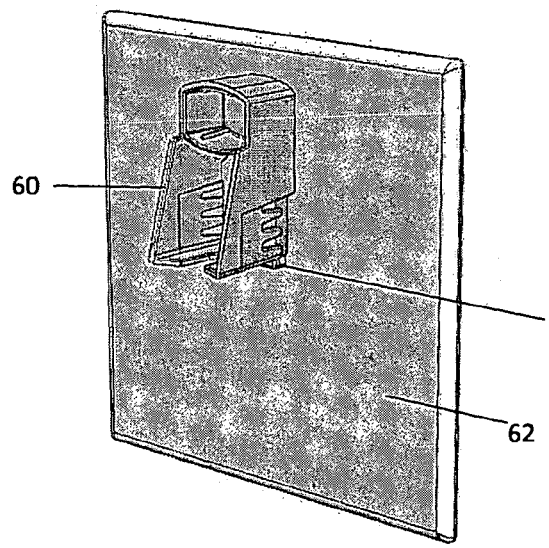
FIG. 8(b) shows a front perspective view of the eighth embodiment of the housing shown in FIG. 8(a) partly attached to the attachment means.
Figure 9B:
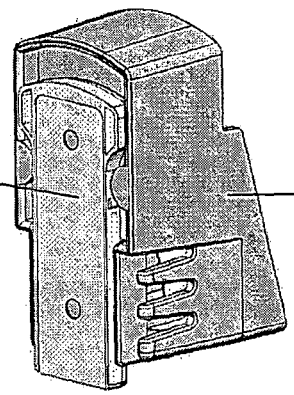
FIG. 9(b) shows a rear perspective view of the eighth embodiment of the housing shown in FIG. 9(a) partly attached to the attachment means.
Figure 8C:
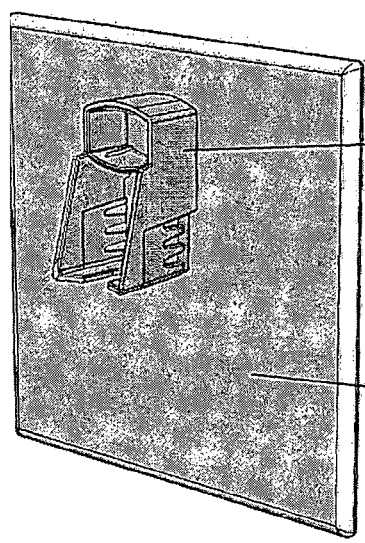
FIG. 8(c) show a front perspective view of the eighth embodiment of the housing shown in FIG. 8(a) securely attached to the attachment means on an attachment surface.
Figure 9C:
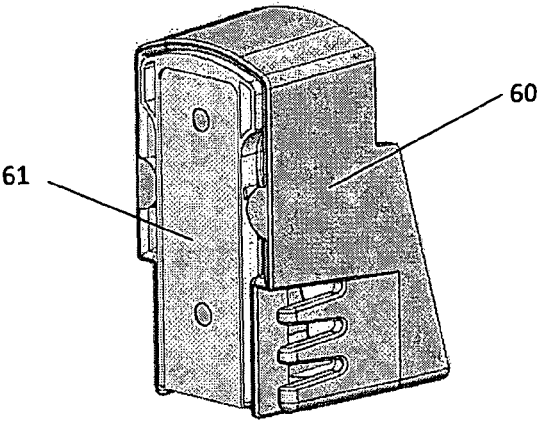
FIG. 9(c) show a rear perspective view of the eighth embodiment of the housing shown in FIG. 9(a) securely attached to the attachment means.
Figures 10A, 10B:
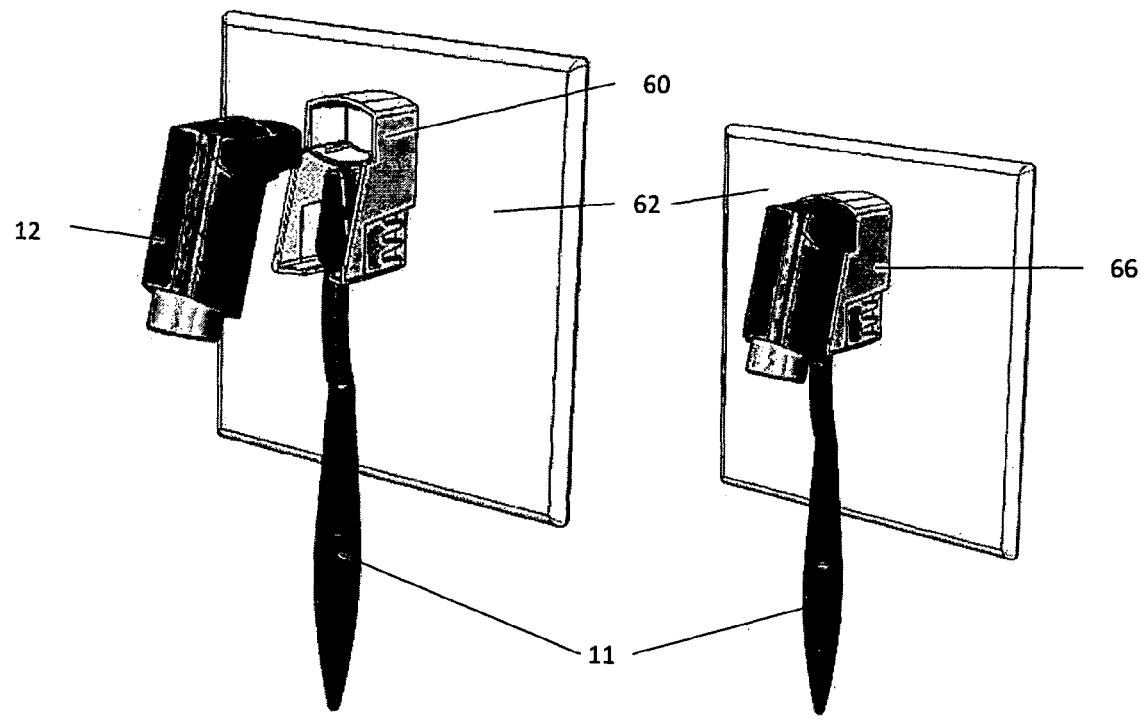
FIG. 10(a) shows a front perspective view of an eighth embodiment of a housing for use with an oral hygiene device securely attached to attachment means in place on an attachment surface holding an oral hygiene device and showing a separate inhaled medication device.
FIG. 10(b) shows a front perspective view of an eighth embodiment of a housing for use with an oral hygiene device securely attached to attachment means in place on an attachment surface holding an oral hygiene device and showing an inhaled medication device engaged with the housing.
Figures 10C, 10D, 10E:
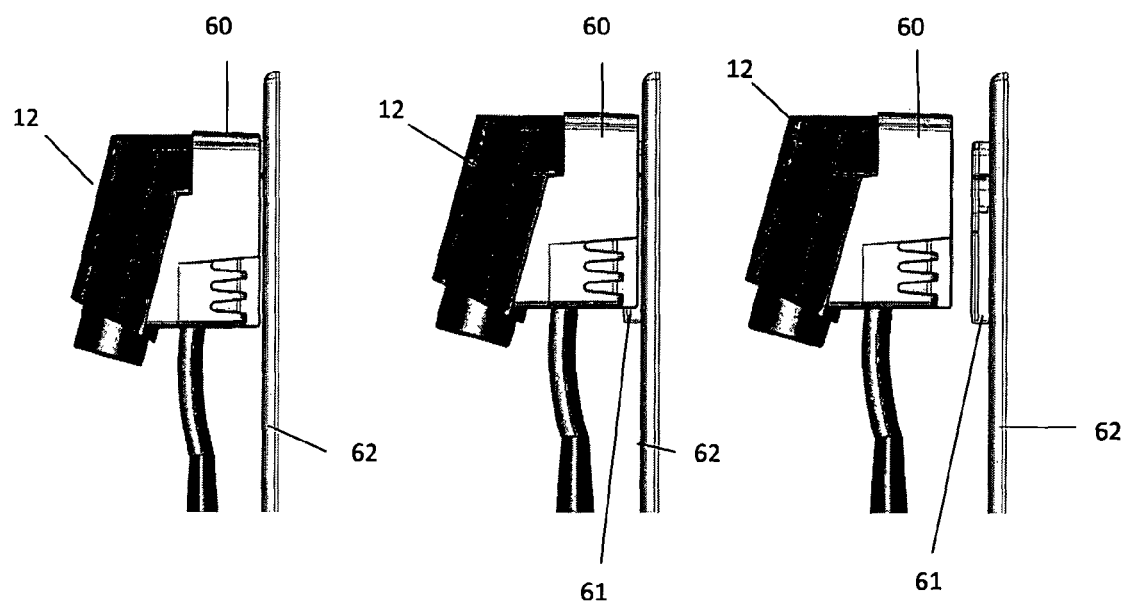
FIG. 10 (c) shows a side view of the eighth embodiment of the housing shown in FIG. 10(b) securely attached to the attachment means on an attachment surface.

As shown in FIGS. 8(a) to 8(c) and 9(a) to 9(c) a separate attachment member 61 is provided that in use is securable to an attachment surface 62 preferably but not exclusively by way of an adhesive bond. The housing 60 is adapted on its rear side to provide lugs 63 and slots 65 that receive complimentary lugs 64 on the attachment member 61 when the housing is positioned over the attachment member as shown in FIGS. 8(b) and 9(b). The housing is then engaged with the attachment member when the housing is moved in a downward motion relative to the attachment member as shown in FIGS. 8(c) and 9(c) such that lugs 64 on the attachment member engage with slots 65. The downward motion of the housing relative to the attachment member 61 is limited by abutments 66 on the attachment member that abut the lugs 63 on the housing 60 when the housing is engaged with the attachment member 61. It is to be appreciated from the FIGS. 10(a) to 10(e) that the assembly of a toothbrush 11, inhaler device 12 and housing 60 can be reversibly engaged with the attachment member 61 that is secured to the attachment surface 62. Similarly the inhaler device 12 and toothbrush 11 can be removed from the housing 60 when the housing 60 is secured to the attachment member (obscured) as shown in FIG. 10(a). As shown in FIGS. 10(c) to 10(e) the assembly of the housing 60, toothbrush 11 and inhaler device 12 can be removed from the attachment member 61 by pushing the assembly upward relative to the attachment member 61 as shown in FIG. 10(d). The assembly can then be reversibly removed from the attachment member 61 as shown in FIG. 10(e).

Manufacture

It is anticipated that the housing embodiments will be made from a plastics material and will be manufactured by a one step injection molding process. The plastics material will need to be of a type that will allow some flexibility to provide the desired snap-fit engagement property and will need to be resilient enough to allow for multiple engagements and disengagements from and into the assembly aspect.

Use of the Housing and Assembly

It is envisaged that an asthma sufferer would use a housing embodiment of the present invention either as a portable device or affixed to a surface, such as a bathroom wall. The user will locate the head of their oral hygiene device into the housing on to the bracket that is shaped and dimensioned to secure the oral hygiene device. The user will then remove the existing cap of their inhaler device and locate the mouthpiece of their inhaler into the mouthpiece engagement portion of the housing. The location of the inhaler in this manner secures the housing, oral hygiene device and inhaler in an assembly. For the asthma sufferer to use their oral hygiene device, the inhaler must first be removed from the assembly and then the oral hygiene device can be removed from its supporting bracket. The act of removing the inhaler from the assembly provides a physical reminder to the asthma sufferer to use the inhaler ahead of using their oral hygiene device. Because it is generally accepted that teeth brushing is a twice daily (morning and night) habit formed over many years for the bulk of the population, the invention provides an additional reminder of the habitual need for an asthma sufferer to take their asthma medication every time they reach for their oral hygiene device.

Advantages

The advantages of the aspects and embodiments provided by this invention, include the close juxtaposition of an oral hygiene device with an inhaler. For asthma suffers this will provide a twice daily reminder when cleaning their teeth of the presence of their asthma inhaler and the need to take their preventive asthma medication. A further advantage is that the nature of the asthma medications is such that good oral hygiene is required after using the inhaler to remove any residual medication from the oral cavity to ensure that the health of the oral cavity is not compromised by the asthma medication. Another advantage is the portability option and relative cheapness of the housing.

The present invention and its embodiments have been described in detail. However, the scope of the present invention is not intended to be limited to the particular embodiments of the invention described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to the embodiments of the invention disclosed herein.

The invention claimed is:

1. A housing comprising:
    a supporting means for receiving and supporting an oral hygiene device,
    and
    an engagement means for receiving and engaging a mouthpiece of an inhaler medication device,
    wherein the supporting means is configured to support the head of the oral hygiene device, and the supporting means includes a recess to accept the handle of the oral hygiene device;
    wherein the supporting means is spaced apart from the engagement means to allow positioning of the head of the oral hygiene device between the supporting means and the engagement means;
    wherein the supporting means and the engagement means are arranged in the housing such that the engagement means is vertically positioned over the supporting means, and such that the recess of the supporting means is closed off by the inhaler medication device when the engagement means is engaged with the mouthpiece of the inhaler medication device;
    this arrangement of the supporting means and the engagement means being such that an oral hygiene device that has been received into the supporting means cannot be removed from the supporting means without first disengaging the mouthpiece of the inhaler medication device from the engagement means; and
    this arrangement of the supporting means and the engagement means thereby providing a physical reminder to a patient to use the inhaler medication device prior to use of the oral hygiene device.

2. The housing as claimed in claim 1, wherein the supporting means is a bracket.

3. The housing as claimed in claim 2 wherein the engagement means is a cavity bounded by four sides, and configured in size and shape to substantially surround the mouthpiece of the inhaler medication device upon engagement with the inhaler medication device.

4. The housing as claimed in claim 2 wherein the engagement means includes one or more ribs or lugs configured to provide a snap fit engagement with the mouthpiece of the inhaler medication device.

5. The housing as claimed in claim 3 wherein the housing is further adapted to include sides that extend between the cavity and the bracket, and that substantially surround the head of the oral hygiene device when the oral hygiene device is in situ on the bracket portion.

6. The housing as claimed in claim 5 wherein the housing further includes ventilation slots to allow air circulation around the head of the oral hygiene device.

7. The housing as claimed in claim 1 wherein the housing includes or receives attachment means to enable attachment of the housing to an attachment surface.

8. The housing as claimed in claim 7 wherein the attachment means includes a rebate region to apply an adhesive strip to the housing.

9. The housing as claimed in claim 7 wherein the housing is adapted to be releasably attached to a separate attachment member wherein the separate attachment member is further adapted to be mounted to an attachment surface.

10. The housing as claimed in claim 1 wherein the inhaler medication device is a metered dose inhaler (MDI).

11. An assembly including a housing, an oral hygiene device and an inhaler medication device, wherein the housing and inhaler medication device together secure the oral hygiene device in the housing such that in use the oral hygiene device cannot be removed from the assembly without first removing the inhaler medication device.

* * * * *